(12) United States Patent
Vaglio et al.

(10) Patent No.: US 11,797,080 B2
(45) Date of Patent: *Oct. 24, 2023

(54) HEALTH SIMULATOR

(71) Applicant: CERNER INNOVATION, INC., North Kansas City, MO (US)

(72) Inventors: Jay Vaglio, Mission, KS (US); Alex Lende, Spirit Lake, IA (US); Eric Wilson, Lee's Summit, MO (US); Mayur Rajendran, Overland Park, KS (US); Taylor Floyd, Kansas City, KS (US); Matt Anderson, Kansas City, MO (US); Anna-Therese Fowler, Leawood, KS (US)

(73) Assignee: Cerner Innovation, Inc., North Kansas City, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 17/740,924

(22) Filed: May 10, 2022

(65) Prior Publication Data

US 2022/0269337 A1 Aug. 25, 2022

Related U.S. Application Data

(63) Continuation of application No. 16/585,513, filed on Sep. 27, 2019, now Pat. No. 11,340,692.

(51) Int. Cl.
*G06F 3/01* (2006.01)
*G06T 19/00* (2011.01)
(Continued)

(52) U.S. Cl.
CPC .............. *G06F 3/011* (2013.01); *A61B 5/744* (2013.01); *G06T 19/006* (2013.01); *G06T 19/20* (2013.01);
(Continued)

(58) Field of Classification Search
None
See application file for complete search history.

(56) References Cited

U.S. PATENT DOCUMENTS 10,354,753 B2 * 7/2019 Lynn ..................... G16H 50/80
10,453,172 B2   10/2019 Kozloski et al.
(Continued)

OTHER PUBLICATIONS

Burykin, Anton, et al. "Toward optimal display of physiologic status in critical care: I. Recreating bedside displays from archived physiologic data." Journal of critical care 26.1 (2011): 105-e1. (Year: 2011).*

(Continued)

*Primary Examiner* — Ryan M Gray
(74) *Attorney, Agent, or Firm* — Kilpatrick Townsend & Stockton LLP

(57) ABSTRACT

Embodiments of the present disclosure relate to systems, methods, and user interfaces that generates and renders virtual environments for display using a VR system (e.g., on a display of a VR headset). Virtual reality is leveraged to create immersive experiences that enables users to experience clinical processes, train staff through new protocols, and gain empathy through a variety of complex scenarios. Initially, contextual information is initially received for an event. Based on the contextual information of the event, data collections is triggered from a clinical system and an environment system for data occurring before and after the event. Utilizing the collected data, a three dimensional modeling of a timeline of event, characters associated with the event, and dialogue corresponding to the event can be recreated. After contributing factors are identified and weighted for the event, a virtual simulation of the event can be created.

20 Claims, 13 Drawing Sheets

(51) Int. Cl.
   *A61B 5/00*    (2006.01)
   *G06T 19/20*   (2011.01)
   *G16H 80/00*   (2018.01)
   *G16H 50/50*   (2018.01)
   *G06F 30/20*   (2020.01)
   *H04L 67/131*  (2022.01)

(52) U.S. Cl.
   CPC ............. *G06F 30/20* (2020.01); *G16H 50/50* (2018.01); *G16H 80/00* (2018.01); *H04L 67/131* (2022.05)

(56) References Cited

U.S. PATENT DOCUMENTS

| | | | | |
|---|---|---|---|---|
| 11,340,692 | B2* | 5/2022 | Vaglio | G06T 19/20 |
| 11,426,603 | B2* | 8/2022 | Kobashi | A61N 5/1037 |
| 2008/0020361 | A1* | 1/2008 | Kron | G09B 23/28 |
| | | | | 434/262 |
| 2010/0167248 | A1* | 7/2010 | Ryan | A61B 34/76 |
| | | | | 434/262 |
| 2016/0246929 | A1 | 8/2016 | Zenati et al. | |
| 2017/0053562 | A1* | 2/2017 | Bova | G09B 23/28 |
| 2018/0122506 | A1* | 5/2018 | Grantcharov | G16H 50/50 |
| 2018/0203238 | A1 | 7/2018 | Smith, Jr. | |
| 2019/0180637 | A1 | 6/2019 | Mealer | |
| 2020/0234487 | A1 | 7/2020 | Clapp et al. | |
| 2020/0279498 | A1 | 9/2020 | Ribeira et al. | |
| 2021/0020060 | A1 | 1/2021 | Hirsch | |
| 2021/0076966 | A1 | 3/2021 | Grantcharov et al. | |
| 2021/0096636 | A1 | 4/2021 | Vaglio et al. | |
| 2023/0038695 | A1* | 2/2023 | Yee | G06F 3/0484 |

OTHER PUBLICATIONS

Barjis, Joseph, "Healthcare simulation and its potential areas and future trends", SCS M&S Magazine 2.5, 2011, 7 pages.

Rall, "Simulation and patient safety: The use of simulation to enhance patient safety on a systems level", Current Anaesthesia & Critical Care 16.5, 2005, pp. 273-281.

* cited by examiner

HEALTH SIMULATOR

CROSS-REFERENCE SECTION

This application is a continuation of prior application Ser. No. 16/585,513 (filed Sep. 27, 2019), which is incorporated herein by reference in its entirety.

BACKGROUND

In today's clinical space, there are many costly simulation tools and services. These services struggle with providing an immersive experience that is affordable. In the consumer space, access to clinical content that can assist specific conditions in an engaging and effective manner is difficult to attain.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces that generates and renders virtual environments for display using a virtual reality (VR) system (e.g., on a display of a VR headset). More particularly, embodiments of the present disclosure leverage virtual reality to create immersive experiences that are engaging and memorable for staff and patients in a variety of complex scenarios. This enables users to experience clinical processes, train staff through new protocols, and gain empathy through the complex scenarios using virtual reality. To do so, contextual information is initially received for an event. Based on the contextual information of the event, data collections is triggered from a clinical system and an environment system for data occurring before and after the event. Utilizing the collected data, a three dimensional modeling of a timeline of event, characters associated with the event, and dialogue corresponding to the event can be recreated. After contributing factors are identified and weighted for the event, a virtual simulation of the event can be created using the three dimensional modeling and the weighted contributing factors.

BRIEF DESCRIPTION OF THE SEVERAL VIEWS OF THE DRAWINGS

The present invention is described in detail below with reference to the attached drawing figures, wherein.

DETAILED DESCRIPTION

Figure 1:
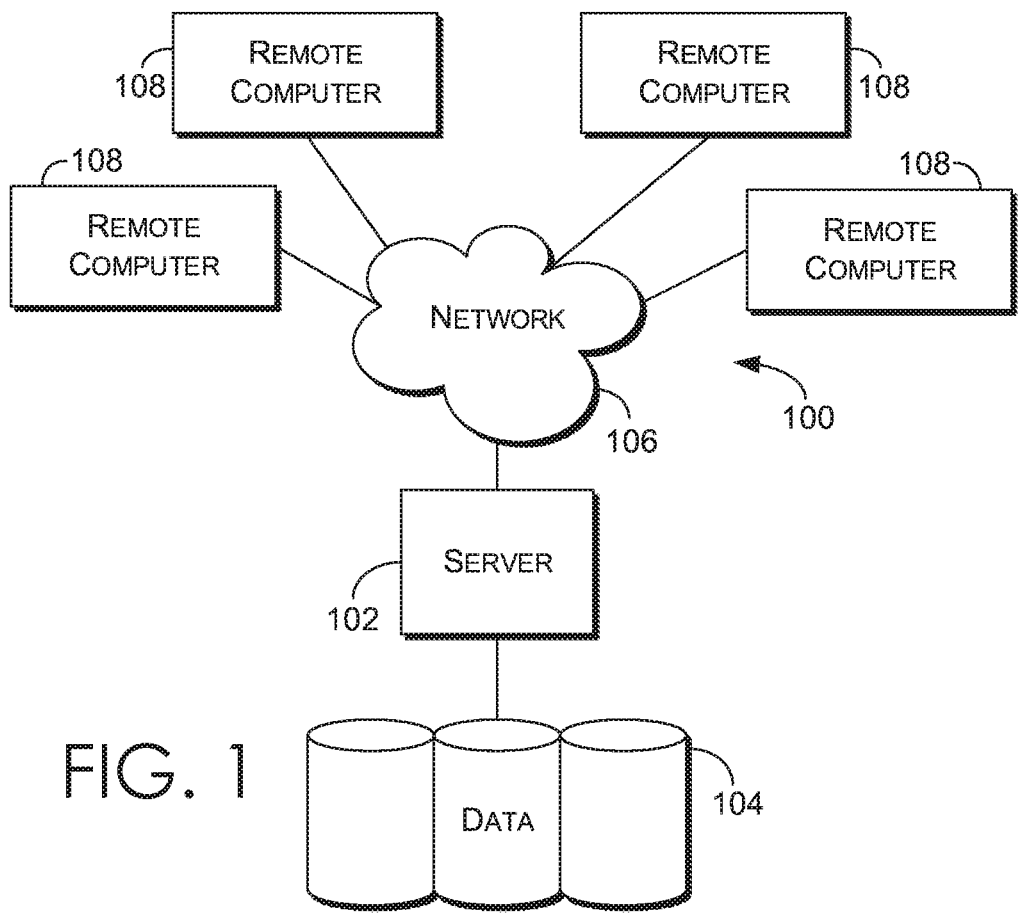
FIG. 1 is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, in today's clinical space, there are many costly simulation tools and services. These services struggle with providing an immersive experience that is affordable. In the consumer space, access to clinical content that can assist specific conditions in an engaging and effective manner is difficult to attain.

Embodiments of the present disclosure relate to systems, methods, and user interfaces that generates and renders virtual environments for display using a VR system (e.g., on a display of a VR headset). More particularly, embodiments of the present disclosure leverage virtual reality to create immersive experiences that are engaging and memorable for staff and patients in a variety of complex scenarios. This enables users to experience clinical processes, train staff through new protocols, and gain empathy through the complex scenarios using virtual reality. To do so, contextual information is initially received for an event. Based on the contextual information of the event, data collection is triggered from a clinical system and an environment system for data occurring before and after the event. Utilizing the collected data (e.g., data from an electronic health record (EHR) and/or the Health Simulator), a three dimensional modeling of a timeline of event, characters associated with the event, and dialogue corresponding to the event can be recreated. After contributing factors are identified and weighted for the event, a virtual simulation of the event can be created using the three dimensional modeling and the weighted contributing factors.

In practice, the Health Simulator improves care experiences and reduces costs. For example, consider an Emergency Department disaster scenario. Today, hospital systems require in-person actors, makeup artists, and space in the Emergency Department to orchestrate large event simulations to train staff. In contrast, the Health Simulator can provide the necessary training ad-hoc to staff in a small setting, while preserving the operations of the Emergency Department. These efficiencies represent clear cost-cutting for training, protocol improvement, and event detection capabilities that is practiced today in many healthcare facilities across the world surrounding topics on disaster relief, mass causality events, and the like.

The Health Simulator integrates health care systems data directly into the simulation. Additionally, the physical/voice interactions and behaviors within the simulation are communicated back to the health care systems. The flow of data to and from the simulation includes, among other things, patient demographic information, a triage score, and real-time system and clinical data. The patient demographic information can be utilized to help guide clinical decisions. The triage score for a patient in the emergency department simulation may be communicated to an EHR of the patient. The real-time system and clinical data can includes things such as patient allergies. This flow of data enables an immersive experience for the user, can be utilized as an aid to the care team outside the simulation (e.g., to adjust protocols), and can be utilized to refine event detection abilities.

Accordingly, one embodiment of the present disclosure is directed to one or more computer storage media having computer-executable instructions embodied thereon that, when executed by a computer, causes the computer to perform operations. The operations include receiving contextual information for an event. The operations also include, based on the contextual information of the event, triggering data collection from a clinical system and environment system for data before and after the event. The operations further include, utilizing the collected data, recreating a three dimensional modeling of a timeline of event, characters associated with the event, and dialogue corresponding to the event. The operations also include identifying contributing factors for the event. The operations further include weighting the contributing factors for the event. The operations also include creating a virtual simulation of the event using the three dimensional modeling and the weighted contributed factors.

In another embodiment, the present disclosure directed to a computerized method. The method comprises utilizing collected data for an event, recreating a three dimensional modeling of a timeline of event, characters associated with the event, and dialogue corresponding to the event. The method also comprises adjusting various factors in a virtual simulation of the event. The virtual simulation is based on the three dimensional modeling. The method further comprises, based on interactions received from a clinician and outcomes during the virtual simulation corresponding to the adjusted various factors of the virtual simulation, modifying a protocol corresponding to the event.

In yet another embodiment, the present disclosure is directed to a system. The system comprises a processor; and a computer storage medium storing computer-usable instructions that, when used by the processor, cause the processor to: receive data from an environment system for a setting; compare the data to previous events corresponding to the setting; based on threshold being exceeded, provide an alert or risk assessment to a user; receive feedback from the user indicating whether the alert or risk assessment adjusted clinician behavior or was inaccurate; and based on the feedback, adjust the threshold to refine detection abilities.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians;

specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
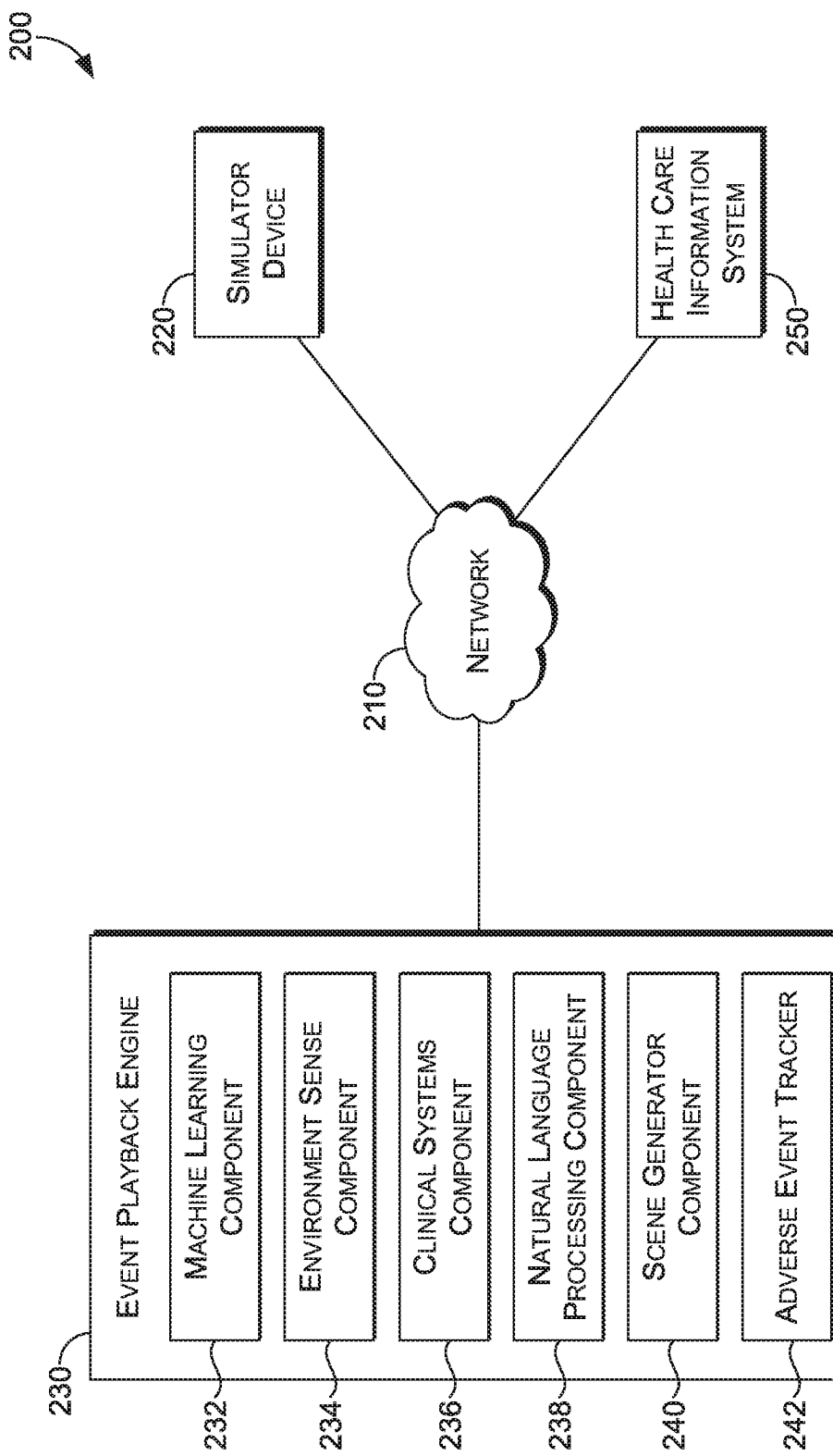
FIG. 2 depicts an exemplary framework of Health Simulator system suitable to implement embodiments of the present invention.

Turning now to FIG. 2, an exemplary framework of an internal server implementation of a Health Simulator system 200 is shown, in accordance with an aspect of the present invention. The Health Simulator system 200 is merely an example of one suitable computing system environment and is not intended to suggest any limitation as to the scope of use or functionality of embodiments of the present invention. Neither should the Health Simulator system 200 be interpreted as having any dependency or requirement related to any single module/component or combination of modules/components illustrated therein.

The Health Simulator system 200 generally operates to generate and render a virtual environment for display using a VR system (e.g., on a display of a VR headset). More particularly, the Health Simulator system 200 leverages virtual reality to create immersive experiences that are engaging and memorable for staff and patients in a variety of complex scenarios. This enables users to experience clinical processes, train staff through new protocols, and gain empathy through the complex scenarios using virtual reality.

As shown in FIG. 2, the Health Simulator system 200 includes, among other components not shown, simulator device 220, event playback engine 230, and health care information system 250, all in communication with one another via a network 210. The network 210 may include, without limitation, one or more local area networks (LANs) and/or wide area networks (WANs). Such networking environments are commonplace in offices, enterprise-wide computer networks, intranets, and the Internet.

In some embodiments, one or more of the illustrated components/modules may be implemented as stand-alone applications. In other embodiments, one or more of the illustrated components/modules may be distributed across multiple event playback engines. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the event playback engines 220 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

Components of the event playback engine 220 may include a processing unit, internal system memory, and a suitable system bus for coupling various system components, including one or more data stores for storing information (e.g., files and metadata associated therewith). The event playback engines 220 typically includes, or has access to, a variety of computer-readable media.

The Health Simulator system 200 is merely exemplary. While the event playback engine 220 is illustrated as a single unit, it will be appreciated that the event playback engine 220 is scalable. For example, the event playback engine 220 may in actuality include a plurality of computing devices in communication with one another. The single unit depictions are meant for clarity, not to limit the scope of embodiments in any form.

As shown in FIG. 2, the event playback engine 230 comprises, in various embodiments a machine learning component 232, an environment sense component 234, a clinical systems component 236, a natural language processing component 238, a scene generator component 240, and an adverse event tracker component 242. In some embodiments, one or more of the components may be implemented as stand-alone applications. It will be understood that the components illustrated in FIG. 2 are exemplary in nature and in number and should not be construed as limiting. Any number of components may be employed to achieve the desired functionality within the scope of embodiments hereof.

Generally, the event playback engine 230 is configured to provide a simulation corresponding to a variety of scenarios that may be utilized for treatment, management, rehabilitation, training, and/or education. For example, the event playback engine 230 may be utilized for process improvements (e.g., modifying protocols), awareness (e.g., adjusting thresholds for detection capabilities), lack of empathy (e.g., effects of reducing resources in a particular scenario), and/or unknown challenges (e.g., emergency scenarios).

Various scenarios may be presented by the event playback engine 230 as a user progresses through the simulation. Initially, a user may be presented immersion therapy. For example, immersion therapy can be utilized to treat acrophobia through exposure to increased elevations. Next, a user may be presented a meditation scenario that elicits deep relaxation, a feeling or presence, and a deeper level of mediation.

The user may progress to an inpatient scenario. In the inpatient scenario, workflow training and process improvements can be facilitated. The inpatient scenario reinforces learning and improves learning retention. Events during the inpatient scenario occur based on user behavior and interactions. Additionally, the event playback engine tracks task completion and records patient event and task completion in a health information system (e.g., an EMR).

In another scenario, the event playback engine 230 provides a therapy scenario. In the therapy scenario, a user's voice is recorded and the user switches perspective between the patient and the clinician. This enables the user, for example, to prepare for an actual in-person counseling session.

Finally, the event playback engine 230 provides an emergency scenario. The emergency scenario provides a high stress, fast paced scenario that does not require space, cost, time, or personnel resources that live emergency training exercises otherwise require.

In this way, the event playback engine 230 provides a number of scenarios. Because the Health Simulator system 200 is integrated with various health information system components, these scenarios can be utilized for training, modifying protocols, and improving detection capabilities. As described above, the event playback engine 230 comprises, in various embodiments a machine learning component 232, an environment sense component 234, a clinical systems component 236, a natural language processing component 238, a scene generator component 240, and an adverse event tracker component 242.

Machine learning component 232 is generally configured to analyze the flow of data received by the Health Simulator system 200. For example, as the machine learning component 232, a current state of the data is recognized and understood. Based on data from past events, the machine learning component 232 may detect a particular event. Machine learning component 232 may additionally adjust the fidelity of assessments or conclusions based on feedback from a user. Guidance may be interjected by machine learning component 232 with confidence scoring received from the user. In some embodiments, machine learning component 232 may manage weights corresponding to actions, sequences, factors, and/or impact of the event. Machine learning component 232 may additionally make predictions based on previous learning.

Environment sense component 234 is generally configured to collect environment data. The environment system data may include data from cameras, sound collection devices, technological systems, protocol or process comparison, temperature, humidity, light, day, time, astronomy, spatial observation, and the like. The environment data may be utilized by scene generator component 240 to recreate a particular setting or make adjustments to a particular setting for a simulation.

Clinical systems component 236 is generally configured to collect clinical systems data from health care information system 250. The clinical systems data may include documentation, communication, workflows, staffing, capacity management, population comparison, treatment outcomes, history, laboratory results, medications, procedures data, examination data, and the like. The environment system data may include data from cameras, sound collection devices, technological systems, protocol or process comparison, temperature, humidity, light, day, time, astronomy, spatial observation, and the like. The clinical systems data may be utilized by scene generator component 240 to recreate a clinical event or make adjustments to a clinical event for a simulation.

Natural language processing component 238 is generally configured to analyze audio collected by environment sense component 234. Natural language processing component 238 may analyze tone or sentiment, summarize collected audio, segment the audio by topic, identify errors, and/or tag parts of speech. Each of these actions may be utilized by scene generator component 240 to recreate a clinical event or make adjustments to a clinical event for a simulation.

Scene generator component 240 is generally configured to recreate or make adjustments to various simulations and scenarios. To do so, scene generator component 240 receives data from the various components. Utilizing this data, scene generator component 240 builds various components for the scenario. For example, scene generator component 240 recreates characters and space dynamics within the scenario. Additionally, scene generator component 240 recreates emotion, interpretation, and errors. Scene generator component 240 also creates perspective dashboards and incorporates variability impact metrics within the scenario. Once all the components necessary for the scenario have been recreated, scene generator component finalizes the simulation and provides narration and the simulation can be replayed by a simulator device 220.

Adverse event tracker component 242 is generally configured to detect adverse events that can be utilized to recreate various scenarios. To do so, adverse event tracker component 242 logs events and self-assessments, provides mortality and morbidity support, analyzes risk for events, maps workflows to the events, determines an impact to care and/or outcome scoring, and categorizes contributing factors for the various events. Each of these items may be utilized to modify various factors of an event within a simulation.

Figure 3:
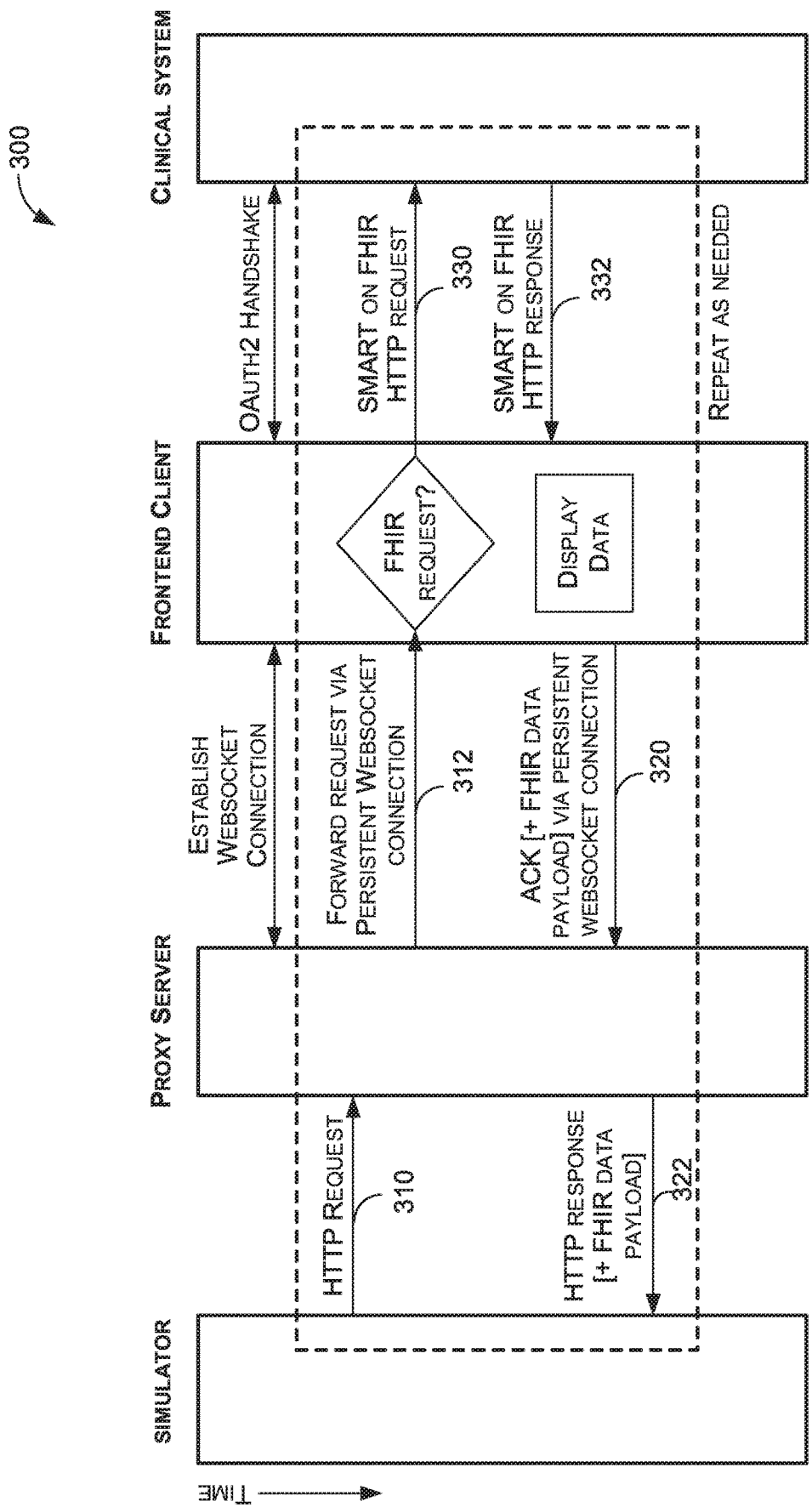
FIG. 3 depicts an exemplary data transactional diagram of a heath simulator system suitable to implement embodiments of the present invention.

Referring now to FIG. 3, an exemplary data transactional diagram 300 of a heath simulator system is shown, in accordance with embodiments of the present invention. Generally, the diagram 300 illustrates the method in which data is pulled and shared with the Health Simulator system. For clarity, the Health Simulator can be deployed to any number of platforms (e.g., personal computer, web, mobile, etc.). As illustrated, a user may be instructed 310, 312 to complete a task in the simulation. Once the user has completed the task in the simulation, data may be pulled from the simulation 320, 322. Additionally, data may be pulled from a variety of clinical systems (e.g., patient allergies or patient demographics) 330, 332 and used in the simulation. Based on user interactions via SMART or FHIR standards, data may also be written to the clinical systems, as needed.

With reference to FIGS. 4-10, illustrative screen displays 400, 500, 600 . . . 1000 of embodiments of the present invention are shown. It is understood that each of the illustrative screen displays are connected logically, such that they comprise a user interface designed for providing a Health Simulator. The screen displays may appear in any order and with any number of screen displays, without regard to whether the screen display is described or depicted herein. The screen displays provide tools that enable health simulation, in accordance with embodiments of the present invention.

Figure 4:
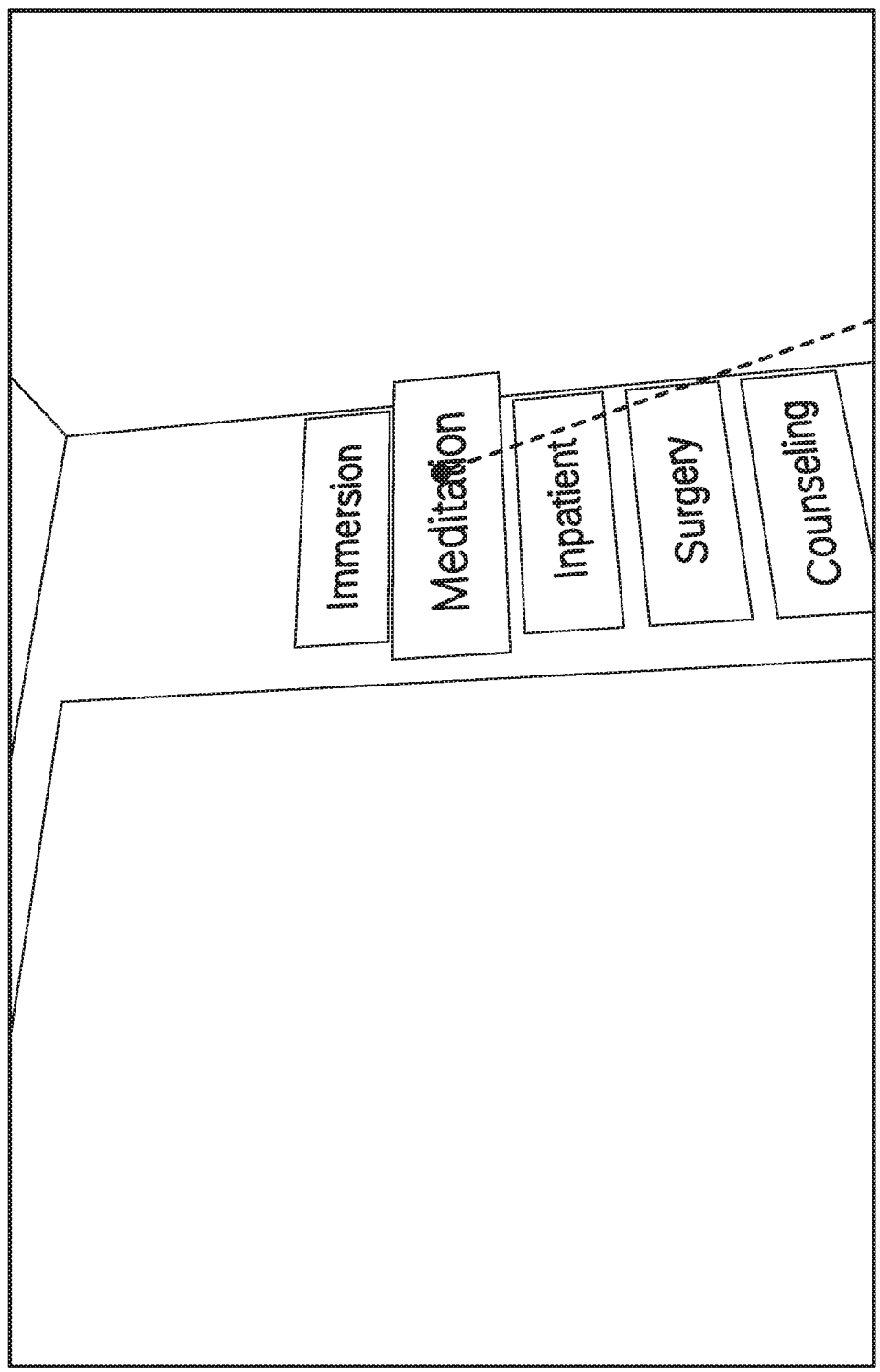
FIG. 4 depicts an illustrative screen display of a scenario selection for a Health Simulator system suitable to implement embodiments of the present invention.

Referring initially, to FIG. 4, an illustrative screen display 400 of a scenario selection for a Health Simulator system suitable to implement embodiments of the present invention is provided. As shown, the scenarios are selectable from an elevator-like display within the simulator. The elevator-like display allows an engaging and scalable manner that facilitates selecting a scenario. A similar elevator-like display can also support small scale training, notifications, and result details from completed scenarios. It should be appreciated that any number of scenarios may be utilized in embodiments of the present invention. For example, the Health Simulator system may include, in some embodiments, scenarios (e.g., a pediatric pain management scenario comprising a flyer game that prompts the patient to look slightly to the left or right and destroy asteroids or other objects) designed to distract a patient from a painful or mundane procedure.

Figure 5:
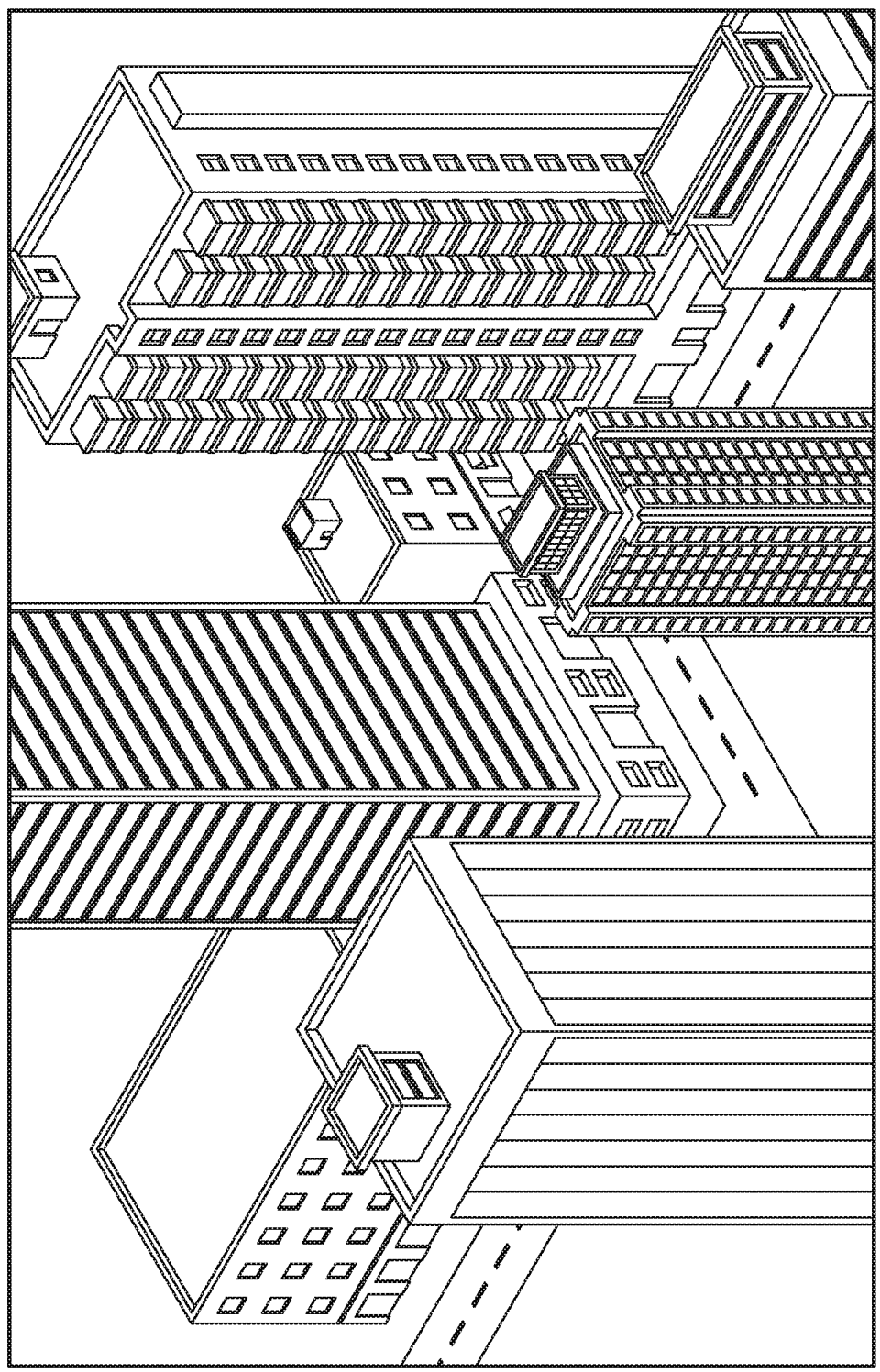
FIG. 5 depicts an illustrative screen display of an immersion therapy scenario for a Health Simulator system suitable to implement embodiments of the present invention.

In FIG. 5, an illustrative screen display 500 of an immersion therapy scenario for a Health Simulator system suitable to implement embodiments of the present invention is shown. The display 500 illustrates a snapshot of the in-scenario experience for users that are addressing a fear of heights. In embodiments, the users has the opportunity to progress up five levels within a city scape, at the user's own pace. To illustrate the connectivity between the Health Simulator system and a health information system, a follow-up visit can be automatically scheduled at the completion of the progression, with results provided to the EMR of the user and made available to a clinician.

Figure 6:
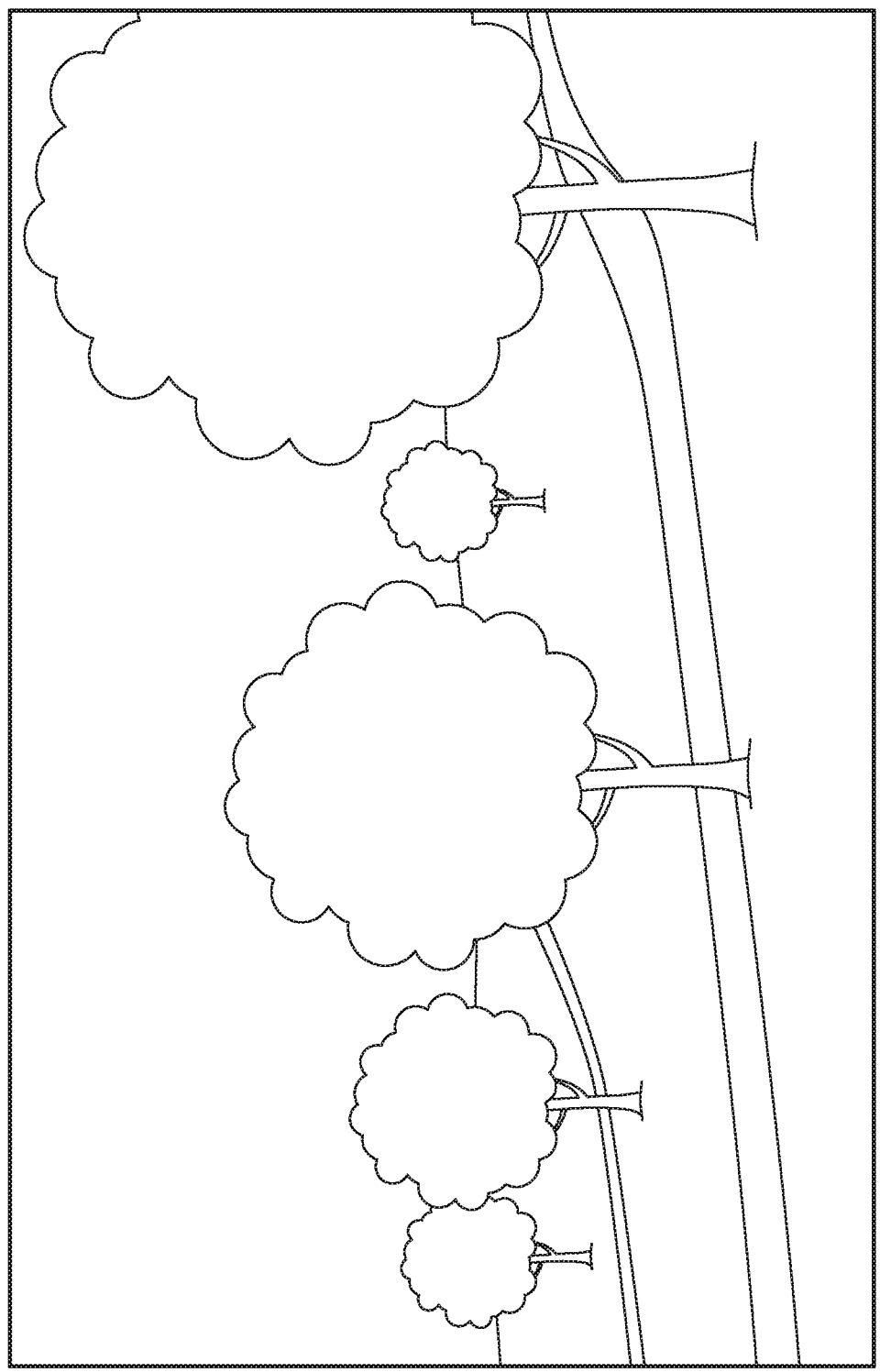
FIG. 6 depicts an illustrative screen display of a meditation scenario for a Health Simulator system suitable to implement embodiments of the present invention.

Next, FIG. 6 depicts an illustrative screen display 600 of a meditation scenario for a Health Simulator system suitable to implement embodiments of the present invention. In the display 600, a snapshot of an in-scenario experience of guided meditation is illustrated. In embodiments, multiple scenes are provided, enabling the user to select a preferred meditation location. In some embodiments, a customized scene may be provided by the user or an EMR of the user to the Health Simulator system. In embodiments, at the conclusion of the guided meditation, a follow-up visit is automatically scheduled. Various results, such as biometric readings as the user engages with the Health Simulator during the simulation may be provided to the EMR of the user and made available to a clinician.

Figure 7:
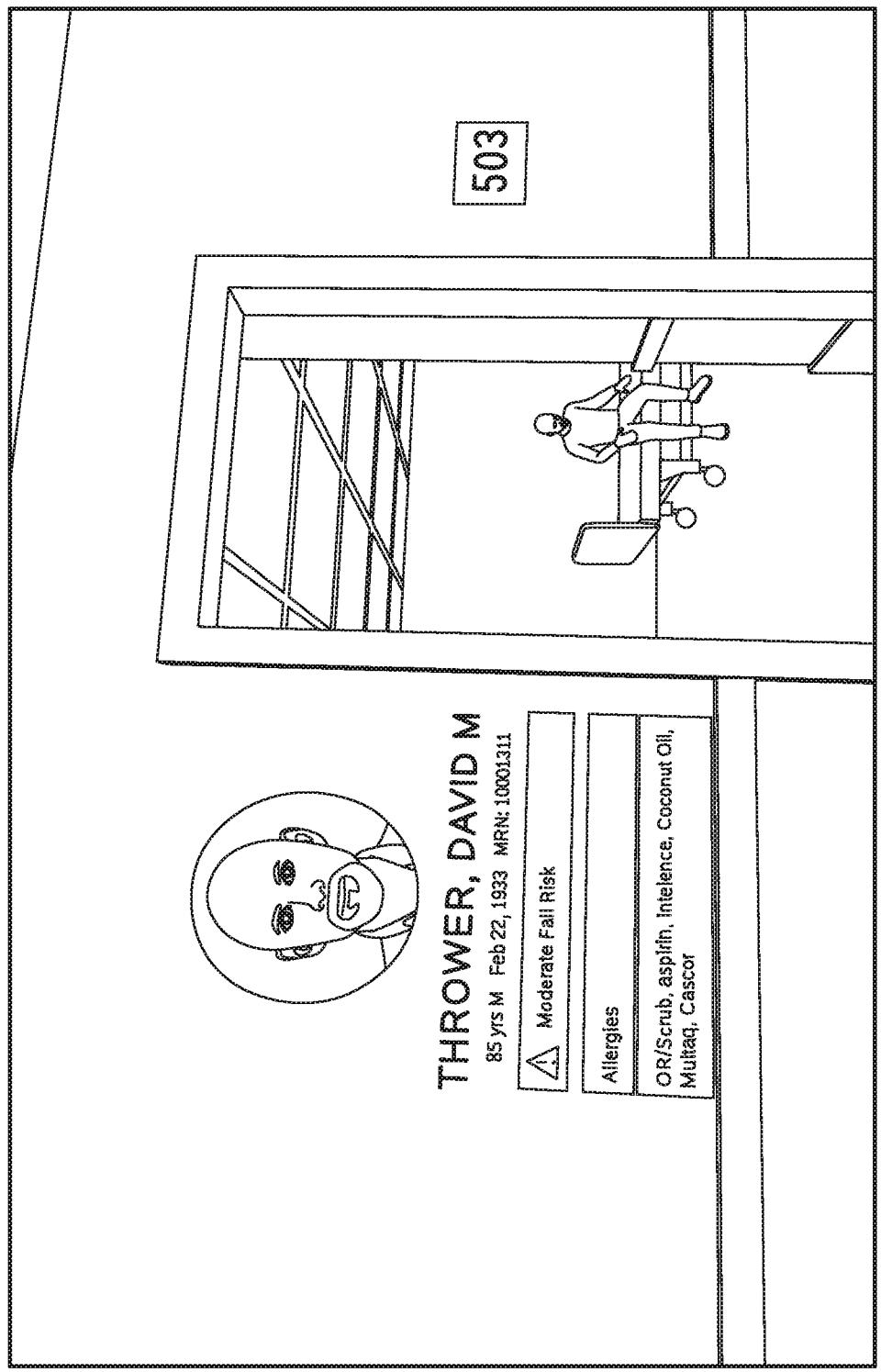
FIG. 7 depicts an illustrative screen display of an inpatient scenario for a Health Simulator system suitable to implement embodiments of the present invention.

Turning now to FIG. 7, an illustrative screen display 700 of an inpatient scenario for a Health Simulator system suitable to implement embodiments of the present invention is depicted. As shown in the display 700, a snapshot of an in-scenario experience for the user during the inpatient simulation is provided. Details shown to the left of the doorway provide actual EMR data being streamed into the simulation. The simulation itself guides the user in completing tasks mimicking a real nursing workflow. As the user completes each task, the details and/or outcomes are communicated to the EMR.

Figure 8:
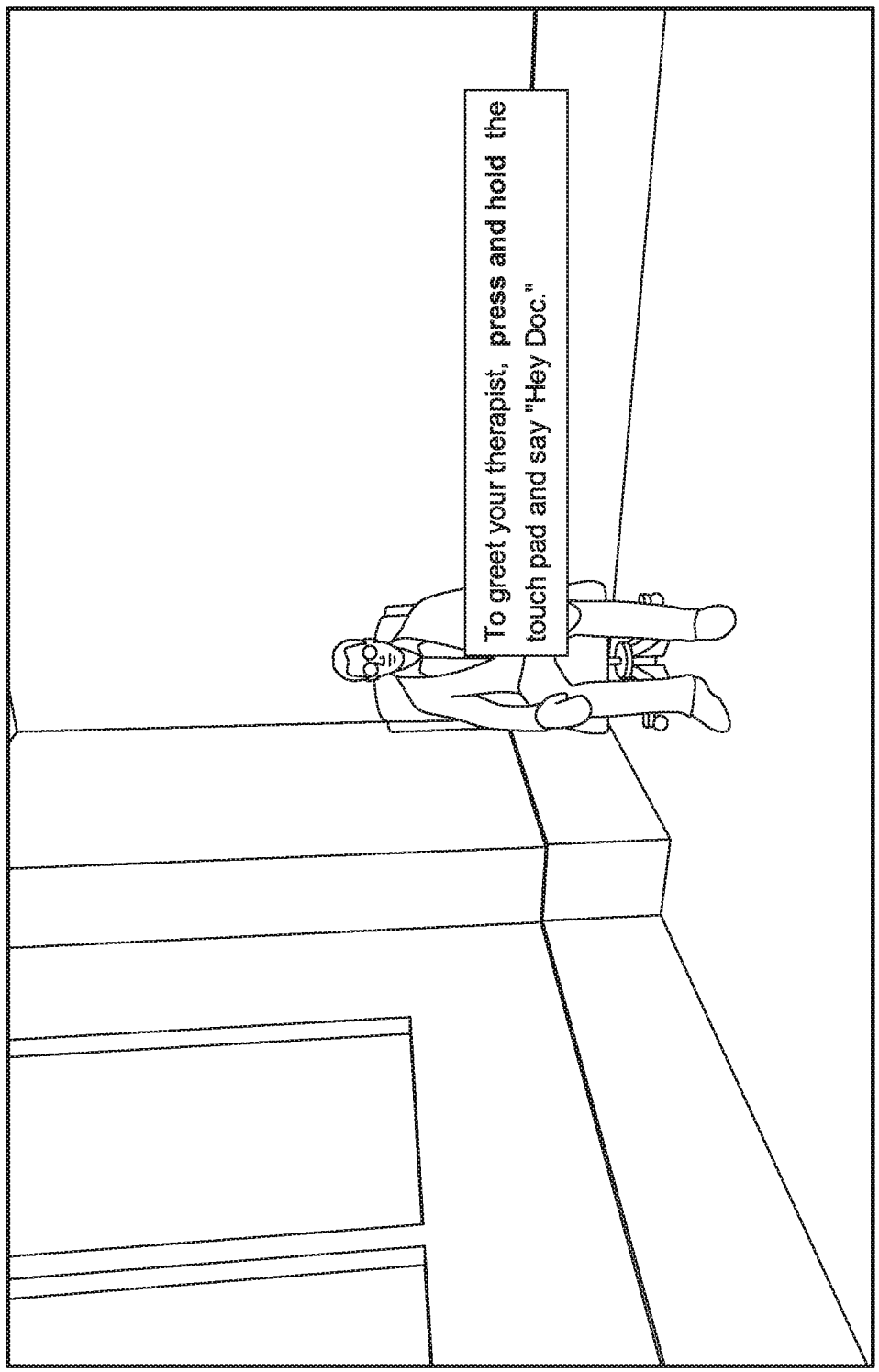
FIG. 8 depicts an illustrative screen display of a self-counseling scenario for a Health Simulator system suitable to implement embodiments of the present invention.

In FIG. 8, an illustrative screen display 800 of a self-counseling scenario for a Health Simulator system suitable to implement embodiments of the present invention is provided. In particular, display 800 illustrates an in-scenario snapshot of a self-counseling scenario. During the simulation, a user can hold a dialogue between a counselor and a patient. In embodiments, both the counselor and the patient roles are played by the user. For example, the user provides a verbal response to an on-screen prompt and the response is recorded and played back to the user once the users switches to the other character. The back and forth conversation facilitates a safe environment for the user to practice sensitive conversations before having the conversation with a clinician. At the conclusion of the session, a follow-up visit is automatically scheduled with a clinician.

Figure 9:
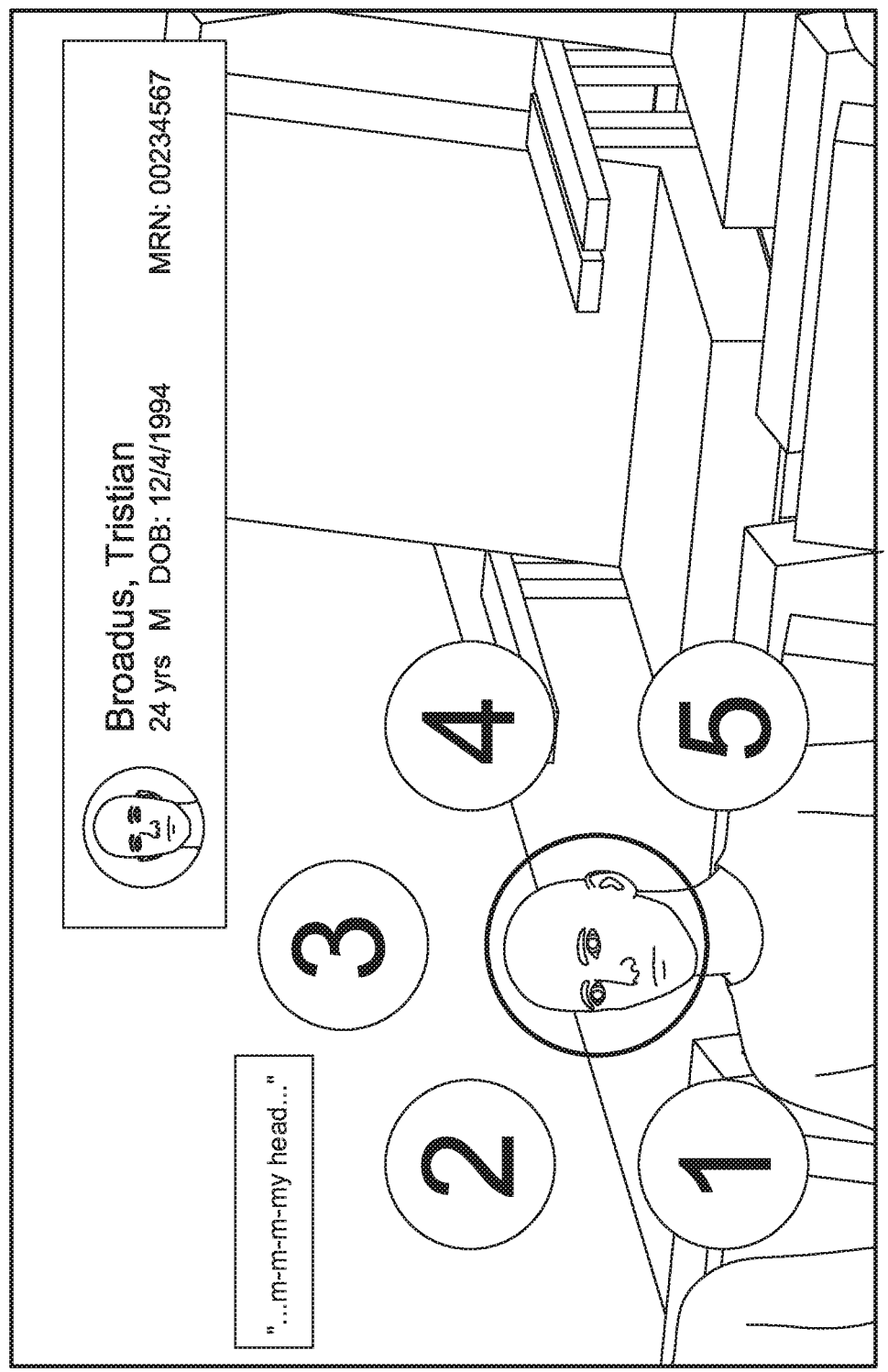
FIGS. 9-10 depicts illustrative screen displays of an emergency scenario for a Health Simulator system suitable to implement embodiments of the present invention.
Figure 10:
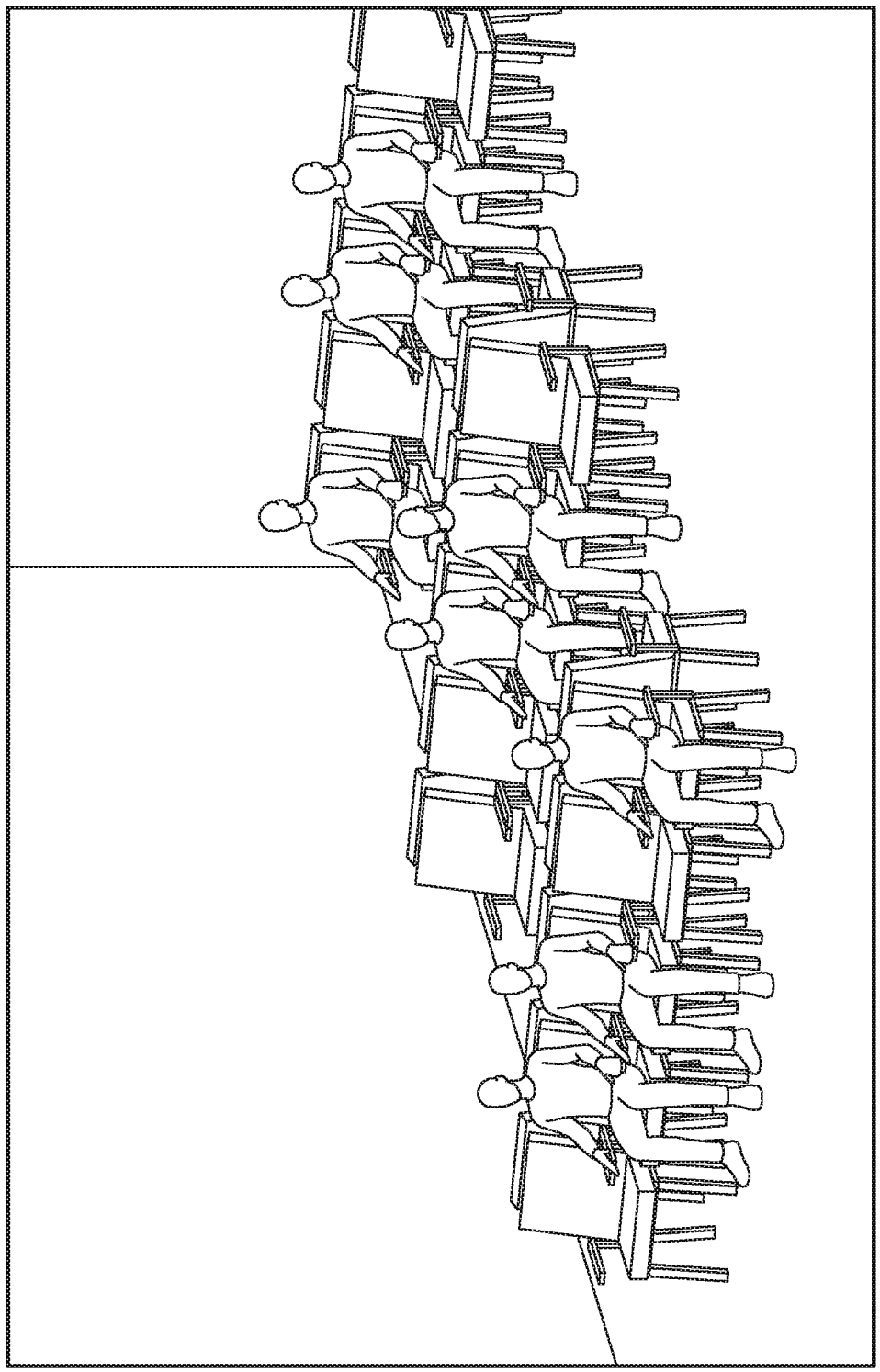

Referring to FIGS. 9-10, illustrative screen displays 900, 1000 of an emergency scenario for a Health Simulator system suitable to implement embodiments of the present invention are shown. As shown in display 900, a user is prompted with a triage scenario and must provide an assessment score for a patient. Display 1000 shows the larger context of the emergency room department being crowded with patients. For example, the scenario may mimic a chaotic environment after a hurricane has hit the area and the user is responsible for triaging patients. As the assessments are completed, the scores may be communicated to the health information system and utilized for training or evaluating clinicians.

Figure 11:
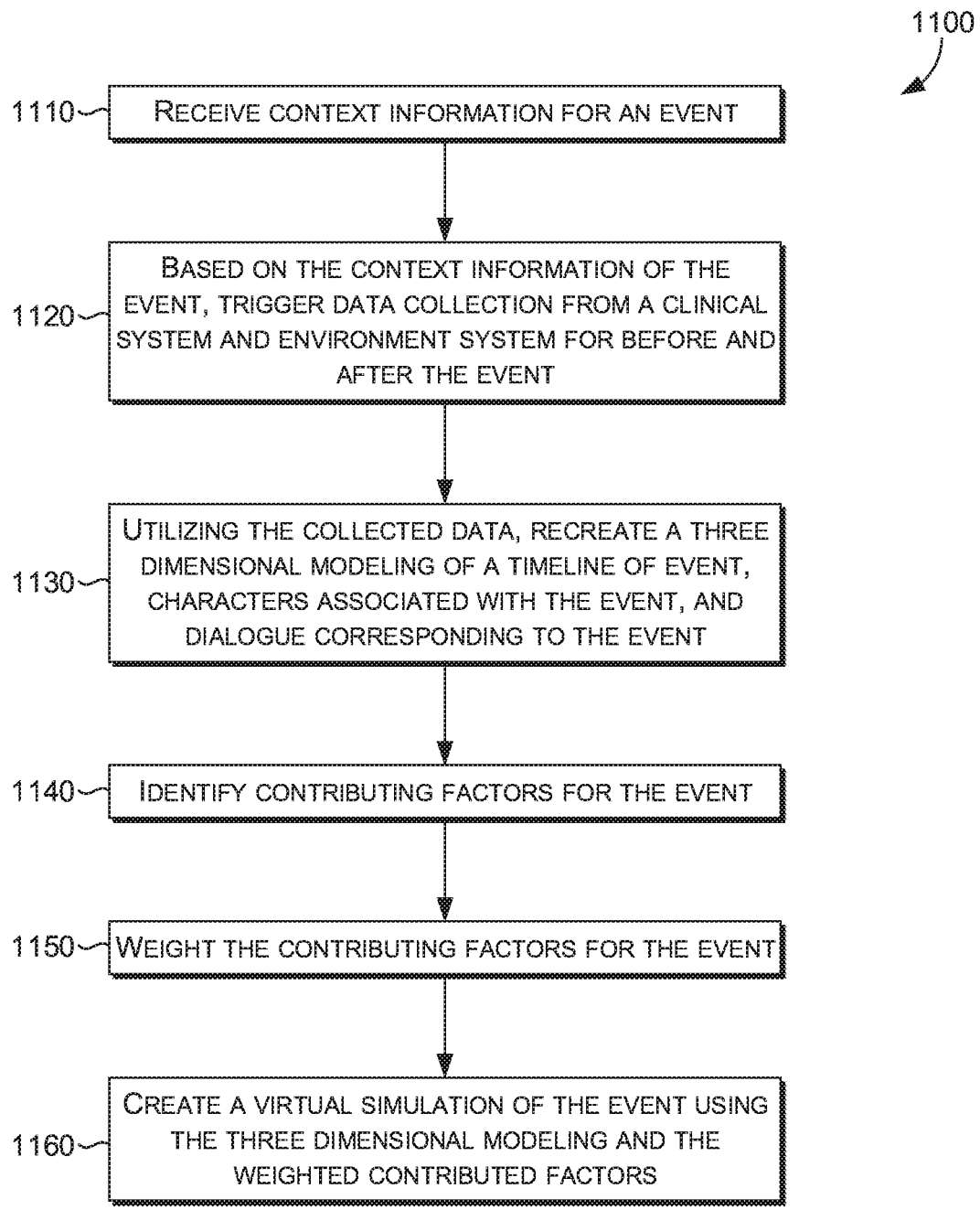
FIG. 11 depicts a flow diagram illustrating a method of creating a virtual simulation for a Health Simulator system, in accordance with an embodiment of the present invention.

Turning now to FIG. 11, a flow diagram is provided illustrating a method 1100 creating a virtual simulation for a Health Simulator system, in accordance with embodiments of the present invention. Method 1100 may be performed by any computing device (such as computing device described with respect to FIG. 1) with access to a Health Simulator system (such as the one described with respect to FIG. 2) or by one or more components of Health Simulator system.

Initially, at step 1110, contextual information for an event is received. The contextual information may include a variety of data points. For example, the contextual information may include physical space data collected via audio sensors, autonomous robots, or other room sensors. Additionally or alternatively, the contextual information may include electronic health record data collected from an electronic health record. Additionally or alternatively, the contextual information may include adverse event data. Additionally or alternatively, the contextual information may include patient safety data.

At step 1120, based on the contextual information of the event, data collection from a clinical system and environment system is triggered for data before and after the event. For example, the clinical systems data may include documentation, communication, workflows, staffing, capacity management, population comparison, treatment outcomes, history, laboratory results, medications, procedures data, examination data, and the like. The environment system data may include data from cameras, sound collection devices, technological systems, protocol or process comparison, temperature, humidity, light, day, time, astronomy, spatial observation, and the like.

Utilizing the collected data, at step 1130, a three dimensional modeling of a timeline of event, characters associated with the event, and dialogue corresponding to the event is created. Contributing factors for the event are identified, at step 1140. After the contributing factors for the event are weighted, at step 1150, a virtual simulation of the event is created, at step 1160, using the three dimensional modeling and the weighted contributed factors.

In some embodiments, the virtual simulation is provided to the user via a virtual simulation device. The user may be enabled to change perspectives among the characters during the virtual simulation (e.g., from clinician to patient, from one clinician type to another, and the like). Additionally, the contributing factors of the event may be adjusted to create alternative scenarios for the virtual simulation.

In some embodiments, based on outcomes of the virtual simulation, a protocol corresponding to the event may be modified. In other embodiments, resources corresponding to the event may be reallocated based on outcomes of the virtual simulation. In yet other embodiments, alerts or thresholds corresponding to the event may be modified based on outcomes of the virtual simulation. Additionally or alternatively, a follow-up visit with a clinician or a follow-up virtual simulation may be scheduled based on outcomes of the virtual simulation.

Figure 12:
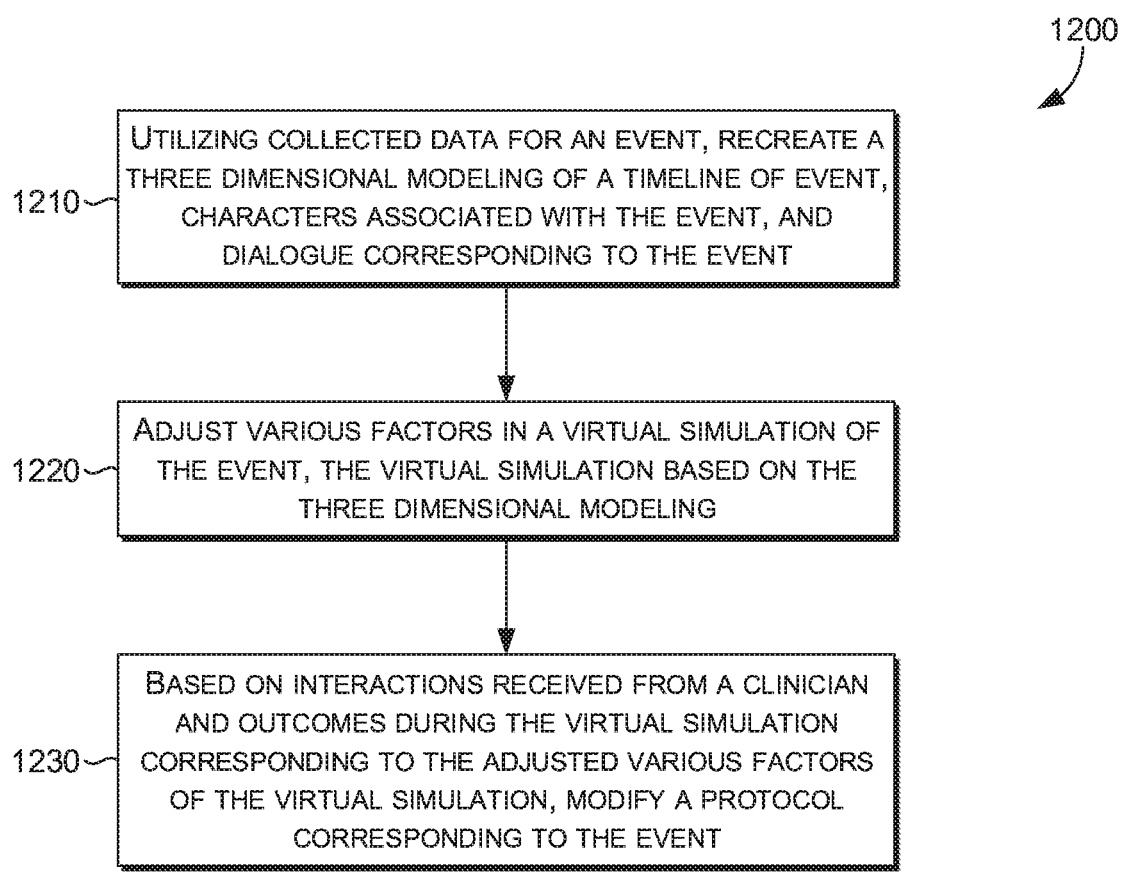
FIG. 12 depicts a flow diagram illustrating a method of modifying protocols using a Health Simulator system, in accordance with an embodiment of the present invention.

In FIG. 12, a flow diagram is provided illustrating a method 1000 of modifying protocols using a Health Simulator system, in accordance with an embodiment of the present invention. Method 1200 may be performed by any computing device (such as computing device described with respect to FIG. 1) with access to Health Simulator system (such as the one described with respect to FIG. 2) or by one or more components of the Health Simulator system.

Initially, at step 1210, utilizing collected data for an event, a three dimensional modeling of a timeline of event, characters associated with the event, and dialogue corresponding to the event is recreated. The collected data may one or more of: physical space data collected via audio sensors, autonomous robots, or other room sensors, electronic health record data collected from an electronic health record, adverse event data, or patient safety data.

At step 1220, various factors are adjusted in a virtual simulation of the event. For example, the adjusted factors may include resource allocation (e.g., a number of clinicians made available for a particular type of adverse event). The virtual simulation is based on the three dimensional modeling. In some embodiments, a user is enabled to change perspectives among the characters associated with the event during playback of the virtual simulation. Based on interactions received from a clinician and outcomes during the virtual simulation corresponding to the adjusted various factors of the virtual simulation, a protocol corresponding to the event is modified, at step 1230.

In embodiments, the protocol may be modified using machine learning techniques. Additionally or alternatively, the virtual simulation may be recorded to expose insights into processes, errors, or near misses. The insights into processes, errors, and near misses of the recording may then be utilized to modify the protocol corresponding to the event.

Figure 13:
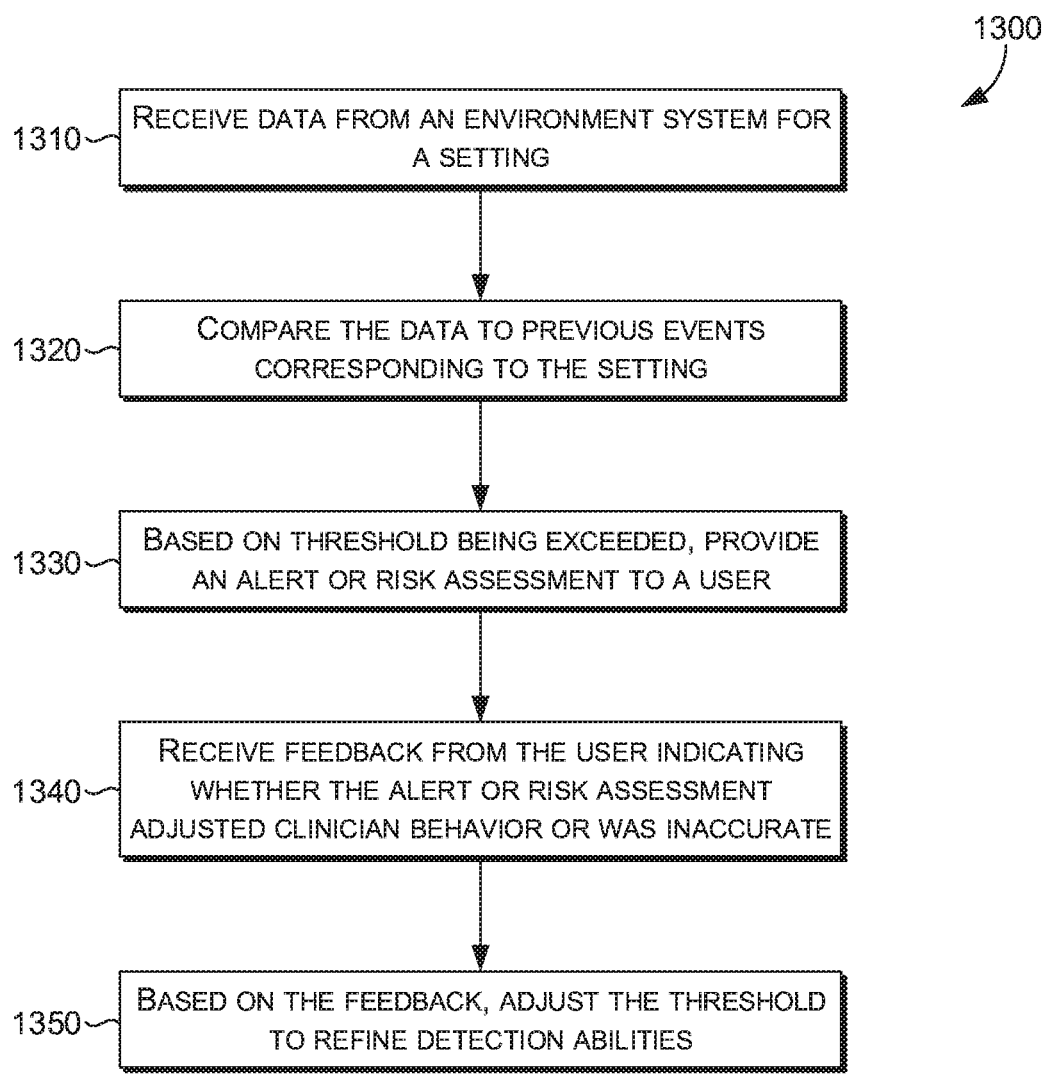
FIG. 13 depicts a flow diagram illustrating a method of adjusting thresholds to refine detection abilities using a Health Simulator system, in accordance with an embodiment of the present invention.

Referring now to FIG. 13, a flow diagram is provided illustrating a method 1300 for generating a soundtrack utilizing live data corresponding to an information system, in accordance with embodiments of the present invention. Method 1300 may be performed by any computing device (such as computing device described with respect to FIG. 1) with access to an Health Simulator system (such as the one described with respect to FIG. 2) or by one or more components of the Health Simulator system.

Initially, at step 1310, data is received from an environment system for a setting. The setting may include a location within a healthcare facility (e.g., an emergency department).

The environment system data may include data from cameras, sound collection devices, technological systems, protocol or process comparison, temperature, humidity, light, day, time, astronomy, spatial observation, and the like.

At step 1320, the data is compared to previous events corresponding to the setting. The comparison helps the Health Simulator system detect adverse events. Based on a threshold being exceeded, at step 1330, an alert or risk assessment is provided to a user. At step 1340, feedback is received from the user indicating whether the alert or risk assessment adjusted clinician behavior or was inaccurate. Based on the feedback, at step 1350, the threshold is adjusted to refine detection abilities.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computerized method comprising:
utilizing collected data for an event, recreating a three dimensional modeling of a timeline of event, characters associated with the event, and dialogue corresponding to the event;
adjusting various factors in a virtual simulation of the event, the virtual simulation based on the three dimensional modeling and presented to a clinician via a virtual simulation device; and
based on interactions received from the clinician and outcomes during the virtual simulation corresponding to the adjusted various factors of the virtual simulation, reallocating resources outside the virtual simulation corresponding to the event.

2. The computerized method of claim 1, further comprising receiving contextual information for the event.

3. The computerized method of claim 2, further comprising, based on the contextual information of the event, triggering data collection from a clinical system and environment system for data before and after the event.

4. The computerized method of claim 1, further comprising identifying contributing factors for the event.

5. The computerized method of claim 4, further comprising weighting the contributing factors for the event.

6. The computerized method of claim 5, further comprising creating the virtual simulation of the event using the three dimensional modeling and the weighted contributing factors.

7. The computerized method of claim 1, wherein adjusting the various factors in the virtual simulation of the event enables alternative scenarios to be created for the virtual simulation.

8. The computerized method of claim 1, further comprising enabling the clinician to change perspectives among the characters during the virtual simulation.

9. The computerized method of claim 1, further comprising modifying a protocol corresponding to the event based on outcomes of the virtual simulation.

10. The computerized method of claim 1, further comprising modifying alerts or thresholds corresponding to the event based on outcomes of the virtual simulation.

11. The computerized method of claim 1, further comprising automatically scheduling a follow-up visit with the clinician or a follow-up virtual simulation based on outcomes of the virtual simulation.

12. The computerized method of claim 1, wherein the collected data includes: physical space data collected via audio sensors, autonomous robots, or other room sensors; electronic health record data collected from an electronic health record; adverse event data; or patient safety data.

13. One or more computer storage media having computer-executable instructions embodied thereon that, when executed by a computer, causes the computer to perform operations, the operations comprising:
   utilizing collected data for an event, recreating a three dimensional modeling of a timeline of event, characters associated with the event, and dialogue corresponding to the event;
   adjusting various factors in a virtual simulation of the event, the virtual simulation based on the three dimensional modeling; and
   based on interactions received from a clinician and outcomes during the virtual simulation corresponding to the adjusted various factors of the virtual simulation, modifying alerts or thresholds outside the virtual simulation corresponding to the event.

14. The media of claim 13, wherein the alerts or thresholds are modified using machine learning.

15. The media of claim 13, wherein the collected data includes one or more of: physical space data collected via audio sensors, autonomous robots, or other room sensors, electronic health record data collected from an electronic health record, adverse event data, or patient safety data.

16. The media of claim 13, further comprising receiving contextual information for the event.

17. The media of claim 16, further comprising, based on the contextual information of the event, triggering data collection from a clinical system and environment system for data before and after the event.

18. The media of claim 13, wherein the collected data includes: physical space data collected via audio sensors, autonomous robots, or other room sensors; electronic health record data collected from an electronic health record; adverse event data; or patient safety data.

19. A system comprising:
   a processor; and
   a computer storage medium storing computer-usable instructions that, when used by the processor, cause the processor to:
   utilize collected data for an event, recreating a three dimensional modeling of a timeline of event, characters associated with the event, and dialogue corresponding to the event;
   adjust various factors in a virtual simulation of the event, the virtual simulation based on the three dimensional modeling; and
   based on interactions received from a clinician and outcomes during the virtual simulation corresponding to the adjusted various factors of the virtual simulation, automatically scheduling a follow-up visit with the clinician or a follow-up virtual simulation.

20. The system of claim 19, further comprising:
   receiving contextual information for the event;
   based on the contextual information of the event, triggering data collection from a clinical system and environment system for data before and after the event;
   identifying contributing factors for the event;
   weighting the contributing factors for the event; and
   creating the virtual simulation of the event using the three dimensional modeling and the weighted contributing factors.

* * * * *